(12) United States Patent
Ostrovsky

(10) Patent No.: US 6,895,270 B2
(45) Date of Patent: May 17, 2005

(54) OPTICAL SCANNING AND IMAGING METHOD

(75) Inventor: Isaac Ostrovsky, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 237 days.

(21) Appl. No.: 10/100,924

(22) Filed: Mar. 20, 2002

(65) Prior Publication Data

US 2002/0091325 A1 Jul. 11, 2002

Related U.S. Application Data

(62) Division of application No. 09/376,376, filed on Aug. 18, 1999, now Pat. No. 6,381,490.
(60) Provisional application No. 60/097,043, filed on Aug. 19, 1998.

(51) Int. Cl.[7] .................................................. A61B 6/00
(52) U.S. Cl. ........................ 600/476; 600/478; 600/173
(58) Field of Search ................................ 600/476, 478, 600/182, 160; 385/8; 359/245, 322, 324

(56) References Cited

U.S. PATENT DOCUMENTS

| | | | |
|---|---|---|---|
| 3,084,488 A | 4/1963 | Eden ........................ 359/316 |
| 4,882,619 A | 11/1989 | Hasegawa et al. .......... 348/337 |
| 4,902,088 A | 2/1990 | Jain et al. ..................... 385/8 |
| 5,061,048 A | 10/1991 | Hayden et al. ............. 359/315 |
| 5,064,257 A | * 11/1991 | Shinoda et al. ............... 359/10 |
| 5,252,180 A | * 10/1993 | Sang et al. .................. 216/18 |
| 5,363,128 A | 11/1994 | Andrews ..................... 346/108 |
| 5,498,869 A | 3/1996 | Appel et al. |
| 5,603,687 A | 2/1997 | Hori et al. ................... 600/166 |
| 5,714,240 A | * 2/1998 | Gupta et al. ................. 428/209 |
| 5,776,174 A | 7/1998 | Van Tassel ................... 607/89 |
| 6,134,003 A | 10/2000 | Tearney et al. ............. 356/345 |
| 6,169,594 B1 | 1/2001 | Aye et al. .................... 349/195 |
| 6,381,490 B1 | * 4/2002 | Ostrovsky ................... 600/478 |

FOREIGN PATENT DOCUMENTS

| | | |
|---|---|---|
| JP | 62 250427 | 10/1987 |
| WO | 92/16865 | 10/1992 |
| WO | 98/38907 | 9/1998 |

OTHER PUBLICATIONS

"Optical Properties," page from Melles Griot Catalog (Date Unknown).
Petrov D.V., "Guided and radiation modes of a graded–index waveguide with defocusing nonlinearity," 1996 Optics Communications, 128: 223–228.

* cited by examiner

*Primary Examiner*—Shawna J. Shaw
(74) *Attorney, Agent, or Firm*—Finnegan Henderson Farabow Garrett & Dunner, L.L.P.

(57) ABSTRACT

A method for imaging an object is disclosed. The method may include transmitting light in a predetermined wavelength range through an optical transmitter to a prism, applying an electromagnetic field to the prism, and passing said light through the prism. The prism may be configured to have an index of refraction that varies with changes in the applied electromagnetic field and that remains substantially constant with changes in wavelength of light over the predetermined wavelength range such that said light exiting from said prism deflects at a substantially controlled angle.

20 Claims, 3 Drawing Sheets

OPTICAL SCANNING AND IMAGING METHOD

This is a division of application Ser. No. 09/376,376, filed Aug. 18, 1999, now U.S. Pat. No. 6,381,490, and claims benefit of 60/097,043 filed Aug. 19, 1998, incorporated herein by reference.

FIELD OF THE INVENTION

The present invention relates to an optical scanning and imaging system. More specifically, the invention relates to a scanning and imaging device that utilizes scanning components without mechanical motion, and is particularly suited for use in medical imaging.

BACKGROUND OF THE INVENTION

A variety of imaging techniques are used for the medical diagnosis and treatment of patients. Ultrasound imaging represents a prevalent technique. Ultrasound uses sound waves to obtain a cross-sectional image of an object. These waves are radiated by a transducer, directed into the tissues of a patient, and reflected from the tissues. The transducer also operates as a receiver to receive the reflected waves and electronically process them for ultimate display.

Another imaging technique is referred to as Optical Coherence Tomography (OCT). OCT uses light, as opposed to sound waves, to obtain a cross-sectional image of tissue. The use of light allows for faster scanning times than occurs in ultrasound technology. The depth of tissue scan in OCT is based on low coherence interferometry. Low coherence interferometry involves splitting a light beam from a low coherence light source into two beams, a sampling beam and a reference beam. These two beams are then used to form an interferometer. The sampling beam hits and penetrates the tissue, or other object, under measurement, and then reflects from the tissue, carrying information about the reflecting points from the surface and the depth of tissue. The reference beam hits a reference reflector, such as, for example, a mirror or a diffraction grating, and reflects from the reference reflector. The reference reflector either moves or is designed such that the reflection occurs at different distances from the beam splitting point and returns at a different point in time or in space, which actually represents the depth of scan. The time for the reference beam to return represents the desirable depth of penetration of tissue by the sampling beam.

When the reflected beams meet, intensities from respective points with equal time delay form interference. A photodetector detects this interference and converts it into electrical signals. The signals are electronically processed and ultimately displayed, for example, on a computer screen or other monitor.

Obtaining a cross-sectional image of an object involves scanning in both the axial and lateral direction. Typical visual frame rates used in filming moving objects are on the order of 30 Hz. Therefore, to image a moving object, such as a beating heart, for example, a scanner system must be capable of scanning approximately 90,000 data points (assuming 300 data points in both the lateral and axial directions of the object, which is typical for an imaging area of $1\times10^{-4}$ mm$^2$) in $\frac{1}{30}$ of a second. However, to accomplish lateral scanning, many OCT systems utilize reciprocally-moving mechanical parts to move the beam of light across the object being imaged. These moving parts often cannot move quickly enough to complete a lateral scan in the requisite time required by the visual frame rate. Thus, imaging of moving objects, such as a beating heart, will be incomplete from frame to frame. Additionally, the use of such parts creates other obstacles to achieving effective scanning. For example, the inertia of moving parts, and their acceleration and deceleration, causes a non-uniform speed of scan and a reduced speed of data acquisition. Furthermore, vibrations associated with the moving parts may result in additional electronic noise which negatively affects the resolution of scanned images.

Design and manufacture of an effective scanning device utilizing moving parts in combination with medical tools such as, for example, a catheter, also proves difficult. For instance, it is very difficult to control precisely the motion of parts on a tip of a catheter. Furthermore, moving parts generally require more space, thus resulting in an increase in the overall size of the device. For catheters and other similar medical devices, such an increase in size is undesirable.

Certain scanner systems used in the communications industry exploit the ability of certain materials to change properties (such as refractive index) when subjected to the application of an electromagnetic field. These communications scanner systems typically include an optically transparent prism positioned between electrodes. A light beam passing through the prism will be deflected at certain angles depending on the electromagnetic field created by the electrodes and applied to the prism. Because deflection of the light also is a function of wavelength, optimal performance of these scanners requires a monochromatic (single wavelength) light source. These scanning systems therefore typically utilize lasers, which use light having a narrow bandwidth, as the source of light.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention includes an optical scanning system for imaging an object. The system includes an optical transmitter that transmits light to a prism positioned relative to the optical transmitter, with the prism receiving the light transmitted by the transmitter. The prism of the optical scanning system has an index of refraction that varies with changes in an applied electromagnetic field and that remains substantially constant with changes in wavelength of light within a given wavelength range.

According to another aspect of the present invention, a scanning system for imaging body tissue includes a catheter having a distal end and a proximal end and configured for insertion into a body. An optical transmitter extends through the catheter from the proximal end to the distal end and transmits light to a first lens positioned relative to the optical transmitter. The first lens transmits a collimated beam of light to a prism positioned relative to the first lens and made of a material that has an index of refraction that changes with changes in an applied electromagnetic field. A second lens is disposed in an opening in a distal end of the catheter for focusing the light that exits the prism within a predetermined angular range.

According to yet another aspect of the present invention, a method for imaging an object includes transmitting light in a predetermined wavelength through an optical transmitter to a prism and applying an electromagnetic field to the prism. The method further includes passing the light through the prism which is configured to have an index of refraction that changes with the applied electromagnetic field and that remains substantially constant over a predetermined wavelength range of light such that the light that exits the prism deflects at a substantially controlled angle.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the preferred embodiments of the invention and, together with the description, serve to explain the principles of the invention. In the drawings.

DESCRIPTION OF THE PREFERRED EMBODIMENTS

This invention generally pertains to a system, and a related method, for performing imaging of objects, and in particular for medical imaging, that overcomes the problems associated with imaging scanners that use mechanically moving parts. For effective performance, particularly in medical imaging, the system and method must achieve high resolution and scanning rates with a small device.

To accomplish these objectives and to overcome the problems associated with existing devices of this kind, an optical scanning and imaging system for use, for example, in medical imaging, according to a preferred embodiment of the present invention incorporates a prism having an index of refraction that changes as a function of an electromagnetic field applied to the prism. By modifying and controlling the electromagnetic field applied to the prism, the index of refraction of the prism, and thus the angular deflection of the light passing through the prism, also can be controlled. The deflected light beam can then be used as the source for an OCT system. This accomplishes imaging of the depth of an object over a lateral dimension of the object without the need for moving components. Thus, a complete scanning of an object can occur in a time period consistent with visual frame rates of approximately 30 Hz to achieve imaging of moving objects, such as, for example, a beating heart, and nonmoving objects. The prism, a means of generating, controlling, and applying a electromagnetic field to the prism, and a means of transmitting light through the prism are incorporated into a medical device, such as, for example, a catheter. Incorporating the prism into the medical imaging device virtually eliminates the problems of vibrations and inertia caused by using moving parts with such small devices.

An additional aspect of the present invention according to yet another preferred embodiment focuses on the selection of the prism material to be used in the optical scanning and imaging system. Aside from changing as a function of electromagnetic field, a material's index of refraction also changes with the wavelength of incident light. This becomes problematic when using a prism with an OCT imaging system because such OCT imaging generally requires non-monochromatic light sources having a bandwidth of from 25 to 50 nanometers. Such relatively large bandwidths achieve short coherence, which in turn results in high image resolution. However, when using a large bandwidth light source, the various component wavelengths deflect from the prism at different angles, resulting in a relatively wide light beam and degrading image resolution.

Figure 1:
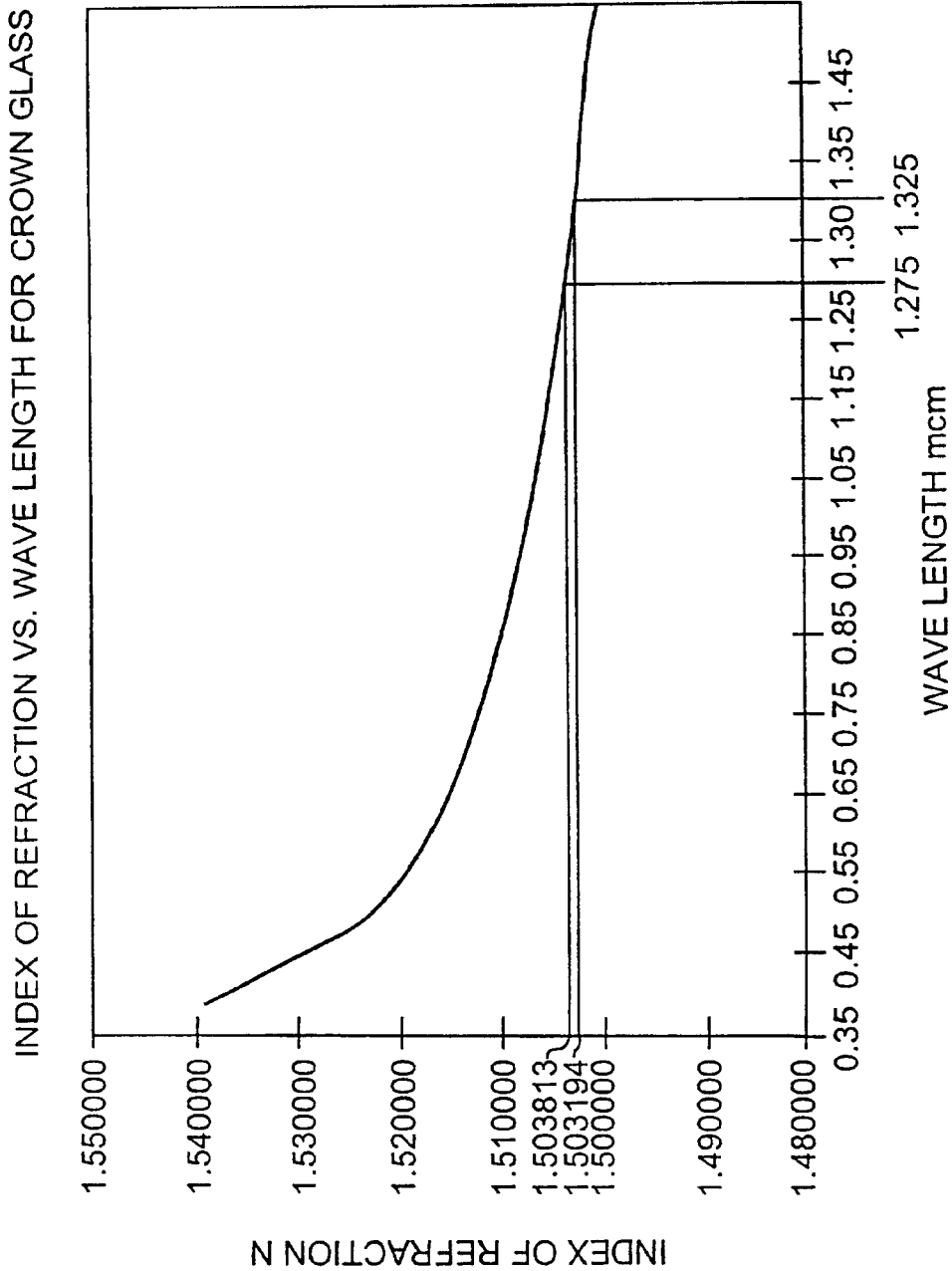
FIG. 1 is a graph of the index of refraction versus wavelength for crown glass.

Therefore, according to another preferred embodiment of the present invention, an optical imaging and scanning system incorporates a prism capable of being subject to an electromagnetic field and made of a material which has an index of refraction that remains substantially constant as the wavelength of incident light changes within a defined wavelength range. Furthermore, by carefully selecting the wavelength range of the light source to be used in the optical scanning and imaging system, refractive indices of the prism, as well as other optical components within the system, also can be confined to a relatively narrow range. An exemplary relationship between incident wavelength and index of refraction that is preferred for the prism material of the present invention is shown in FIG. 1. FIG. 1 illustrates how the index of refraction of crown glass (an example of a glass used in a variety of optics applications) varies with the wavelength of incident light. As shown, the index of refraction changes significantly over smaller ranges of lower wavelength light. However, at ranges of higher wavelength light, for example, between approximately 1275 to 1325 nanometers, the index of refraction remains substantially constant, for example, in a range of approximately 1.503823 to 1.503194.

Additional features that result in the effectiveness of such an imaging device without mechanically moving parts include a coating on optical components to modify and control surface indices of refraction, and optical correcting components, such as a focusing objective lens, to preserve the tightness of focus for a given beam.

Figure 2:
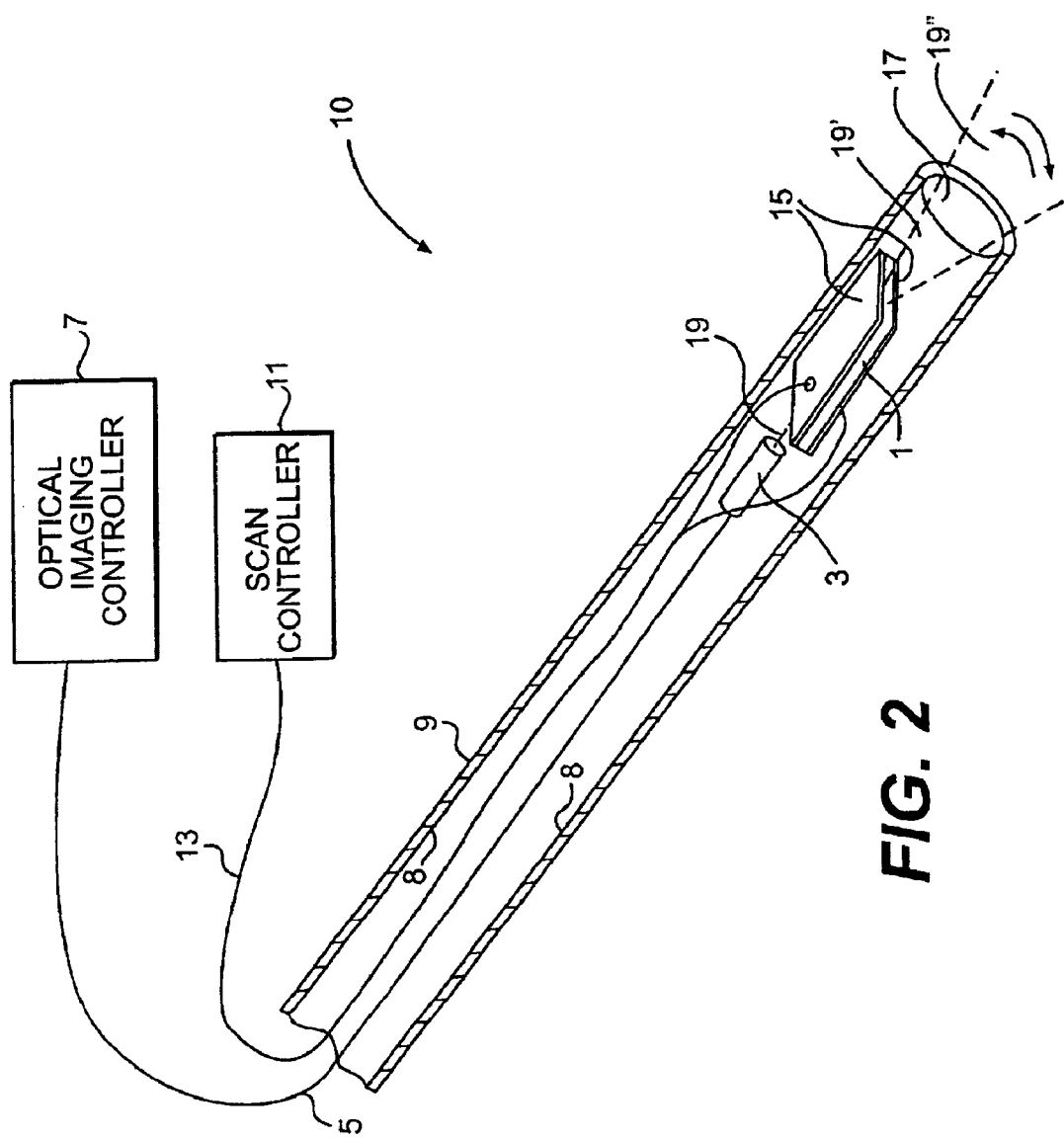
FIG. 2 is a plan view of a preferred embodiment of an optical scanning system according to the present invention, with a cutaway perspective of a catheter housing several of the scanning system's components.
Figure 3:
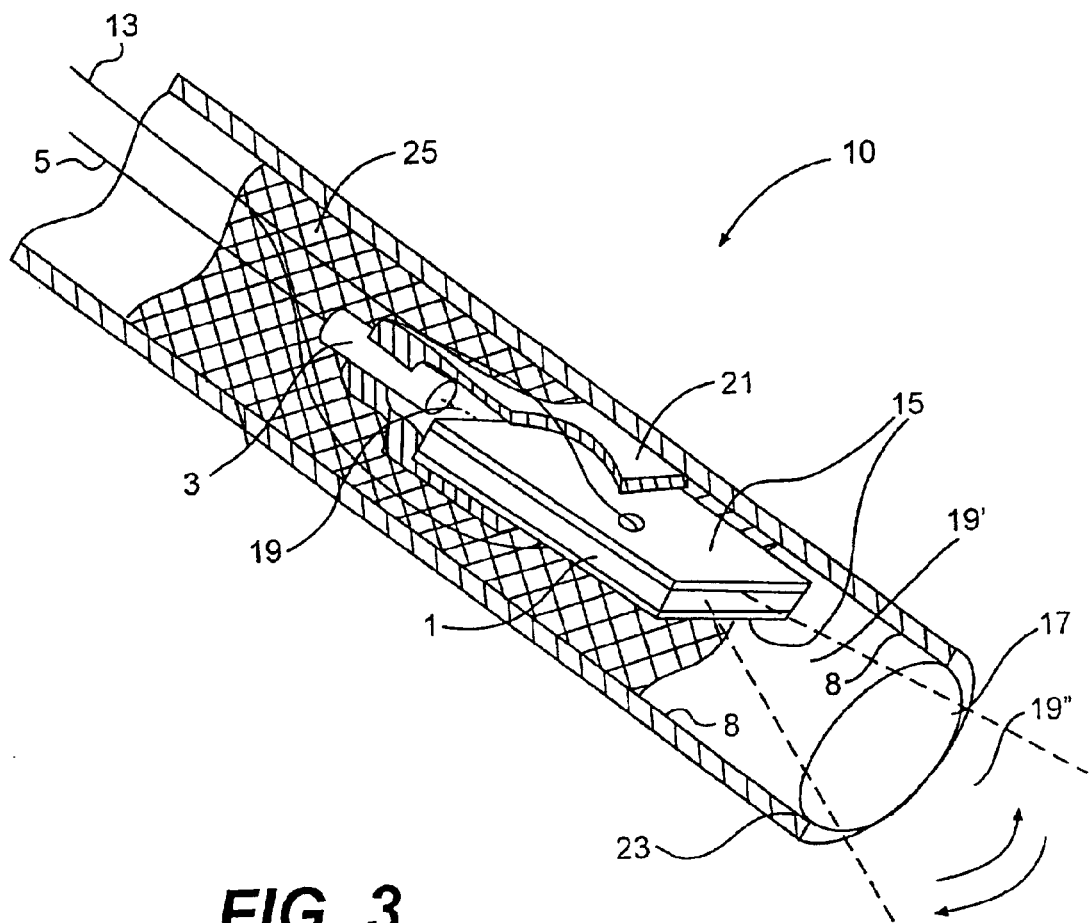
FIG. 3 is a cutaway perspective view of a portion of the catheter of FIG. 2 showing details of the placement of several of the optical scanning system's components within the catheter.

Reference will now be made in detail to the present exemplary embodiments of the invention, examples of which are illustrated in FIGS. 2 and 3. Wherever possible, the same reference numbers will be used throughout the drawings to refer to the same or like parts.

In accordance with a preferred embodiment of the present invention, an optical scanning and imaging system 10 using both optical and electrical energy is provided. System 10 includes an optical imaging controller 7. Optical imaging controller 7 further includes a light source, a light detector, and processing and imaging electronics (not shown). A controller 7 of suitable components and characteristics would be known to one skilled in the art of optical scanning and imaging. Optical imaging controller 7 connects to an optical transmitter, such as an optical fiber 5. Optical fiber 5 extends between optical imaging controller 7, at one end, to a gradient index (GRIN) lens 3, at a distal end. Optical fiber 5 is preferably of the single mode, polarization-maintaining type which is adapted to conduct optical information. However, it is contemplated that other suitable optical transmitters or fibers for carrying optical signals may be used with the system of the present invention.

A deflecting prism 1 according to an embodiment of the present invention is placed adjacent to and spaced from GRIN lens 3 on a side of GRIN lens 3 opposite to the side to which optical fiber 5 connects. Prism 1 is positioned so that it may receive light emitted from lens 3. According to an aspect of the present invention, deflecting prism 1 is made of a material that varies its index of refraction as a function of an applied electromagnetic field. According to another aspect of the present invention, deflecting prism 1 also is made of a material that has a substantially constant index of refraction with changes in wavelengths within a specific wavelength range of incident light. One example of such a material that incorporates both of these properties includes silica with additives of rare earth metals or, for example, lithium-tantalate ($LiTaO_3$) or strontium-barium-niobate (SBN). Such a material exhibits a similar index of refraction versus wavelength characteristic as crown glass shown in FIG. 1. That is, the general shape of the curve will be similar, although precise numeric values may differ. The various additives that are used in combination with the silica will affect these precise values and should be chosen depending on the desired characteristics, for example, incident wavelength range, of the scanning system. Other suitable materials exhibiting similar characteristics also may be used and are within the scope of the present invention.

To apply the electromagnetic field to prism 1, an electrode 15 is placed on each side of prism 1. The electrodes 15 are preferably placed on opposite prism sides that are parallel to the plane of deflection of the light that travels through the prism. A pair of wires 13 each connect at one end to one of the respective electrodes 15. At their other ends, wires 13 connect to a scan controller 11. Scan controller 11 includes a signal generator and amplifier (not shown). Electrical signals, generated in scan controller 11, travel over wires 13 to electrodes 15 to create an electromagnetic field of controlled strength that is applied to prism 1. It is contemplated that both wires 13 and electrodes 15 are made of copper or silver, or other suitable like material capable of conducting electricity and generally known to those having ordinary skill in the art. Electrodes 15 preferably are in the form of thin plates, however other suitable configurations are contemplated and within the scope of the invention. Moreover, any scan controller of suitable components and characteristics known to one skilled in the art of optical scanning and imaging is within the scope of this invention.

In a preferred embodiment of the present invention, an objective lens 17 is disposed on a side of prism 1 opposite to the side where GRIN lens 3 is disposed. When so disposed, objective lens 17 redirects and focuses a beam of light passing through lens 17 to predetermined angular range. Such a lens also aids in reducing scatter of the ultimate imaging beam in order to produce a system having an overall sharper resolution.

As shown in FIGS. 2 and 3, a preferred use of optical scanning and imaging system 10 includes disposing the system within a catheter 9. Accordingly, scan controller 11 and optical imaging system 7 are located outside of catheter 9. Optical fiber 5 and wires 13 extend from optical imaging system 7 and scan controller 11, respectively, into a proximal end of catheter 9 and through catheter 9 to the remaining components of scanning and imaging system 10 located at a distal end of catheter 9.

FIG. 3 illustrates in detail the mounting of optical fiber 5, wires 13, GRIN lens 3, prism 1, and objective lens 17 within catheter 9. A holder 21 secures prism 1 with surrounding electrodes 15 to GRIN lens 3. As shown in the Figure, holder 21 has a substantially U-shaped configuration, with GRIN lens 3 secured to an apex of the U while the legs of the U clamp around outer surfaces of electrodes 15 to hold prism 1. Holder 21, thus, is configured to maintain a predetermined distance between GRIN lens 3 and prism 1. Holder 21 preferably is made from a material that exhibits high rigidity, strength, and insulating properties, such as, for example, polycarbonate or other suitable like material. While FIG. 3 shows holder 21 having a U-shaped configuration, other configurations are contemplated as long as they allow for firm securing of prism 1, electrodes 15, and GRIN lens 3 relative to each other.

A fixing member 25, preferably in the form of potting compound, secures the entire assembly, including optical fiber 5, GRIN lens 3, electrical wires 13, electrodes 15, and holder 21, within catheter 9. Member 25 preferably fills substantially the entire space between the various components and inner walls 8 of catheter 9, and extends along a length of catheter 9 from approximately a distal end of prism 1 to slightly past a proximal end of GRIN lens 3. It is contemplated to use a potting compound such as silicon rubber or epoxy for member 25. However, other suitable like materials also may be used and would be within the scope of the present invention.

Objective lens 17 is secured to the distal opening 18 of catheter 9 using an adhering member 23. Member 23 is preferably in the form of optical adhesive having similar optical properties as the incident beam of light used in conjunction with optical scanning and imaging system 10, while also being capable of sealing the inside of catheter 9 from the penetration of moisture. An example of such an optical adhesive includes an adhesive called "Norland Optical Adhesive 61", supplied by Norland Products, Inc. However, other epoxies or suitable like optical adhesives having the desired properties can be used and would be within the scope of the present invention.

A preferred embodiment of the combined optical scanning system 10 and catheter 9 has the following dimensions so as to be compatible for use with typical endoscopes. Catheter 9 has an outside diameter of approximately 2.7 mm, an inside diameter of approximately 2.3 mm, and a wall thickness of approximately 0.2 mm. Deflecting prism 1 with attached electrodes 15 is approximately 20 mm long, approximately 2.2 mm wide, and approximately 0.5 mm thick. GRIN lens 3 generally has a cylindrical configuration with a diameter of approximately 0.5 mm and a length of approximately 3 to 5 mm. The overall length of the system from a proximal end of GRIN lens 3 to a distal end of objective lens 17 is approximately 40 mm, including gaps between GRIN lens 3 and prism 1, and prism 1 and objective lens 17. These dimensions are meant to be exemplary only. It is contemplated that the various components' dimensions, as well as the overall system dimensions, may vary according to the precise procedure the system is used to perform. For instance, it will be appreciated by persons having ordinary skill in the art that the gap between GRIN lens 3 and prism 1 is not critical and can be as little as zero since a collimated beam of light exits GRIN lens 3. The gap between prism 1 and objective lens 17 depends on the focal length of objective lens 17, which is designed according to actual deflection angular range exhibited by prism 1 and the desired range of angular deflection exiting objective lens 17. The thickness of objective lens 17 also may be determined by desired performance characteristics.

When used for optical scanning and imaging, system 10 works in the following manner. Light is generated by the light source within optical imaging system 7. The wavelength range emitted by the light source is selected as a function of the material used for prism 1. That is, the incident wavelengths must be selected within the range for which the prism material exhibits a relatively constant index of refraction over the entire range. Choosing relatively high wavelengths for the incident light allows for greater penetration of the depth of the object. Thus, it is preferable to select a material for prism 1 that has substantially constant indices of refraction over ranges of relatively high wavelengths.

The radiated light from system 7 is polarized in a plane perpendicular to a plane of scanning and travels along optical fiber 5 and through GRIN lens 3. From GRIN lens 3, the light exits as a collimated beam 19 and enters prism 1. Prism 1 deflects collimated beam of light 19 in an angular direction in the scanning plane. The deflected light beam 19' then enters objective lens 17 which focuses and redirects the beam within a predetermined angular range in order to achieve sharper image resolution.

Light 19" exiting objective lens 17 is then directed to the object to be imaged. The reflected light from the object then enters objective lens 17, goes back through prism 1, GRIN lens 3, and optical fiber 5 to the optical imaging system 7 where it is processed and converted into an image, as described earlier with respect to OCT systems generally. The processed image is then displayed on a computer monitor or other suitable, like display means.

An aspect to the operation of optical scanning and imaging system 10 includes controlling the angle of deflection of light beam 19' exiting deflecting prism 1. As previously discussed, prism 1 is made of a material that has a varying index of refraction with changes in an applied electromagnetic field. Thus, the refractive index of prism 1, as well as the angular deflection of beam 19', can be controlled and modified by controlling and modifying the amplitude and frequency of the electromagnetic field generated between electrodes 15. The signal generator and amplifier of scan controller 11 control the frequency and amplitude of the electromagnetic field, and can be either manually controlled by a user or automatically controlled using systems generally known to those skilled in the art.

It will be apparent to those skilled in the art from consideration of the specification and practice of the invention disclosed herein that various modifications and variations can be made in the optical scanning and imaging system according to the present invention. For example, preferred materials for component parts of the system, including the prism, have been suggested in the specification, but other materials having similar properties could be utilized as well. Also, the sizes and shapes of the various components, including the GRIN lens, the prism, the electrodes and the objective lens of the system may differ from one embodiment to the next depending on, for example, the medical procedure to be performed. Various changes in size and shape may also be necessary depending on the types of objects desired to be imaged and the environments in which the objects are located. Additionally, it is contemplated to use surface coatings on various optical components within the system to alter various properties of those components, including, for example, the index of refraction. Selection of coatings for the desired properties would be obvious to persons having ordinary skill in the art.

Furthermore, although much of the discussion of the optical scanning system according to the present invention focuses on a system used for medical imaging, and particularly for use in medical imaging catheters for use in a lumen of an endoscope or other like device, it is contemplated that the system can be used for other imaging processes and for imaging various objects. These other uses include, for example, other medical applications, including vascular or nonvascular, and non-medical applications.

Therefore, the invention in its broader aspects is not limited to the specific details and illustrative examples shown and described in the specification. It is intended that departures may be made from such details without departing from the true spirit or scope of the general inventive concept as defined by the following claims and their equivalents.

What is claimed is:

1. A method for imaging an object comprising the steps of:
   providing an optical transmitter and a prism in a catheter and placing the catheter in a lumen of an endoscope;
   transmitting light in a predetermined wavelength range through the optical transmitter to the prism;
   applying an electromagnetic field to the prism; and
   passing said light through the prism, the prism being configured to have an index of refraction that varies with changes in the applied electromagnetic field and that remains substantially constant with changes in wavelength of light over the predetermined wavelength range such that said light exiting from said prism deflects at a substantially controlled angle.

2. The method of claim 1, further comprising passing the light from the optical transmitter to a lens, producing a collimated beam of light in the lens, and transmitting the collimated beam of light to the prism.

3. The method of claim 1, further comprising focusing the light within a predetermined angular range after the light exits from the prism.

4. The method of claim 1, further comprising sending light from an optical image controller to the optical transmitter and receiving light reflected from the object being imaged.

5. The method of claim 4, further comprising analyzing the reflected light and forming an image of the object.

6. The method of claim 1, wherein the prism comprises silica.

7. The method of claim 6, wherein the prism further comprises rare earth metals.

8. The method of claim 1, wherein the step of applying the electromagnetic field comprises creating the electromagnetic field between electrodes of the prism.

9. The method of claim 1, wherein the index of refraction of the prism varies with changes in frequency and amplitude of the electromagnetic field applied to the prism.

10. The method of claim 9, further comprising controlling and modifying the amplitude and frequency of the electromagnetic field.

11. A method for imaging an object, comprising:
    providing a medical device having an optical transmitter and a prism, and inserting the medical device into a patient's body;
    transmitting non-monochromatic light in a predetermined wavelength range through the optical transmitter to the prism;
    applying an electromagnetic field to the prism; and
    passing the light through the prism, the prism being configured to have an index of refraction that varies with changes in the applied electromagnetic field and that remains substantially constant with changes in wavelength of light over the predetermined wavelength range such that the light exiting from the prism deflects at a substantially controlled angle.

12. The method of claim 11, further comprising passing the light from the optical transmitter to a lens, producing a collimated beam of light in the lens, and transmitting the collimated beam of light to the prism.

13. The method of claim 11, further comprising focusing the light within a predetermined angular range after the light exits from the prism.

14. The method of claim 11, further comprising sending light from an optical image controller to the optical transmitter and receiving light reflected from the object being imaged.

15. The method of claim 14, further comprising analyzing the reflected light and forming an image of the object.

16. The method of claim 11, wherein the prism comprises silica.

17. The method of claim 16, wherein the prism further comprises rare earth metals.

18. The method of claim 11, wherein the step of applying the electromagnetic field comprises creating the electromagnetic field between electrodes of the prism.

19. The method of claim 11, wherein the index of refraction of the prism varies with changes in frequency and amplitude of the electromagnetic field applied to the prism.

20. The method of claim 19, further comprising controlling and modifying the amplitude and frequency of the electromagnetic field.

* * * * *